United States Patent [19]
Hoffman et al.

[11] Patent Number: 5,034,428
[45] Date of Patent: * Jul. 23, 1991

[54] IMMOBILIZED BIOMOLECULES AND METHOD OF MAKING SAME

[75] Inventors: Allan S. Hoffman; Liang C. Dong, both of Seattle, Wash.

[73] Assignee: Board of Regents of the University of Washington, Seattle, Wash.

[*] Notice: The portion of the term of this patent subsequent to May 9, 2006 has been disclaimed.

[21] Appl. No.: 348,049

[22] Filed: May 4, 1989

Related U.S. Application Data

[63] Continuation of Ser. No. 876,247, Jun. 19, 1986, Pat. No.

[51] Int. Cl.$^5$ .................. C08J 3/28; C12N 11/00; C12N 11/12
[52] U.S. Cl. ............................. 522/5; 204/165; 204/166; 435/179; 435/180; 435/182; 522/87; 524/704; 524/733; 524/744; 526/238.1; 527/201; 527/314
[58] Field of Search ............... 522/5, 87, 89, 87.5; 435/179, 180, 181, 182, 186, 188; 204/165, 166; 527/201, 314; 524/704, 733, 744; 526/238.1

[56] References Cited

U.S. PATENT DOCUMENTS

| | | | |
|---|---|---|---|
| 3,925,157 | 12/1975 | Hamsher | 435/180 |
| 3,959,078 | 5/1976 | Guire | 435/179 |
| 3,989,454 | 11/1976 | Arthur, Jr. et al. | 522/89 |
| 4,193,845 | 3/1980 | Kaetsu et al. | 438/182 |
| 4,194,066 | 3/1980 | Kaetsu et al. | 435/182 |
| 4,272,617 | 6/1981 | Kaetsu et al. | 435/182 |
| 4,310,397 | 1/1982 | Kaetsu et al. | 522/173 |
| 4,379,038 | 4/1983 | Kaetsu et al. | 522/121 |
| 4,436,813 | 3/1984 | Wood et al. | 435/179 |
| 4,451,568 | 5/1984 | Schneider et al. | 522/167 |

OTHER PUBLICATIONS

D. Campbell et al., "The Preparation and Characterization of Some Cellulose Graft Copolymers v. ESR Study of Preirradiation Grafting of Styrene to Cellulose Acetate," J. Polymer Sci., 7, pp. 429-437(1969).
S. Dilli et al., "Radiation-Induced Reactions with Cellulose," Aust. J. Chem., 24, pp. 981-987 (1971).
K. D. N. Lawrence et al., "The Graft Polymerization of Acrylamide Onto Paper Preirradiated with High Energy Electrons," J. Appl. Polymer Sci., 17, pp. 2653-2666 (1973).
K. Matsuzaki et al., "Radiation-Induced Graft Copolymerization of Mixtures of Styrene and n-Butyl Acrylate Onto Cellulose and Cellulose Triacetate," J. Appl. Polymer Sci., 16, pp. 1339-1355 (1972).
S. Munari et al., "Molecular Weights of Grafted Polystyrene Onto $\gamma$-Preirradiated Cellulose Diacetate," J. Appl. Polymer Sci., 14, pp. 807-816 (1970),.
F. S. Radi et al., "Radiation Grafting of Vinyl Monomers Onto Wood Pulp Cellulose II," J. Appl. Polymer Sci., 16, pp. 2685-2696 (1972).
M. U. Sadykov et al., "Radiation-Induced Graft Copolymerization of Vinyl Monomers Onto Cellulose," Proc. Tihany Symp. Radiation Chem., Iobo, ed., pp. 1037-1048 (1971).
T. Yasukawa et al., "Kinetics of Radiation-Induced Grafting Reactions, II. Cellulose Acetate-Styrene Systems," J. Polymer Sci., pp. 2547-2556 (1973).

Primary Examiner—Allan M. Lieberman
Attorney, Agent, or Firm—Seed and Berry

[57] ABSTRACT

A method of biomolecule immobilization is described in which the biomolecule itself or, alternatively, a monomer-conjugated biomolecule, is grafted with free monomer onto a hydrophilic, solid-phase, polymeric substrate which has been pre-irradiated with ionizing radiation. The pre-irradiation step is carried out, preferably at $-78°$ C. in air, while the grafting step is carried out at $0°$ C. in a substantially oxygen-free atmosphere. The technique is applicable to immobilization of a wide variety of biomolecules, such as enzymes, catalysts, hormones, lectins, drugs, vitamins, antibodies, antigens, nucleic acids, DNA and RNA segments, pesticides, dyes and fertilizers. The products may be used for therapeutic or diagnostic applications or bioseparations.

52 Claims, No Drawings

IMMOBILIZED BIOMOLECULES AND METHOD OF MAKING SAME

Cross-Reference to Related Application

This application is a continuation of U.S. application Ser. No. 6,876,247 filed Jun. 19, 1986, U.S. Pat. No. 4,928,048.

TECHNICAL FIELD

The present invention relates to immobilized biologically and chemically active molecules and the method of producing such immobilized molecules generally, and specifically relates to the grafting of biomolecules and free monomers to solid-phase polymeric substrates by pre-irradiating the substrates at low temperatures and post-reacting to attach the active molecules under especially mild conditions.

BACKGROUND ART

Immobilization of chemically and/or biologically active molecules (hereinafter referred to as biomolecules) would be greatly enhanced by the availability of a relatively inert solid-phase, polymeric substrate to which substances, such as enzymes, catalysts, hormones, lectins, drugs, vitamins, antibodies, antigens, nucleic acids, DNA and RNA segments, pesticides, dyes and fertilizers, could be readily and efficiently immobilized under mild conditions so that they would retain high activity. Unfortunately, many processes for attaching biomolecules to polymeric substrates, such as cellulose, require the utilization of relatively high temperatures, high or low pH, catalysts and initiators. These conditions and agents can often irreversibly inactivate or degrade the biomolecule, especially in the case of enzymes, antibodies, and other labile molecules. Yields are also reduced by such harsh prior art methods The prior art teaches that the interaction of ionizing radiation with solid-phase, polymeric substrates leads to the formation of free radicals, some of which are trapped within the polymer matrix. These radicals are polymeric species, since they are formed on the polymeric substrate (e.g. cellulose). These polymeric radicals can be used to initiate a graft copolymerization reaction with hydrophilic monomers and biomolecules under conditions where such molecules can diffuse into the polymer matrix and reach the trapped radical sites.

If the monomer is present during irradiation, then irradiation will also produce radicals in the monomer phase, so that undesirable homopolymers will be formed in addition to the monomer-substrate graft. Also, if the biomolecule is present it may be damaged and deactivated by the radiation. This method of grafting to cellulose has been widely studied, and has been used to graft vinyl monomers onto paper (K. D. N. Lawrence and D. Verdin, *J. Appl. Polymer Sci.* 17:2653, 1973; M. U. Sadykov et al. in "Proc. Tihany Symp. Rad. Chem., 3rd Meeting," Vol. I., J. Dobo (ed.), pp. 1037, 1971; D. Campbell et al., *J. Polymer Sci.* 7:429, 1969). Alternatively, the cellulose may be irradiated before being brought into contact with the monomer. This pre-irradiation technique has also been applied to cellulose (F. S. Radi et al., *J. Appl. Polymer Sci.* 16:2685, 1972; K. D. N. Lawrence and D. Verdin, supra).

Lawrence and Verdin, supra, prepared graft copolymers of acrylamide with paper pre-irradiated at high dose rates available in electron beams in the 200-keV energy region. The temperature of the pre-irradiated cellulose was room temperature, with subsequent grafting of the acrylamide at 20°–60° C. One problem inherent in the Lawrence technique is that the grafting performed subsequently to the pre-irradiation is done at elevated temperatures which are hostile to most biomolecules, especially enzymes and other proteins. Thus, it would be desirable to develop a technique to maximize the copolymerization of the substrate, while providing favorable grafting conditions to allow immobilization of various biomolecules to the pre-irradiated substrate.

In 1972, Hoffman et al. (A. S. Hoffman et al., *Trans. ASATO* 18:10, 1972) immobilized various biomolecules, with and without extension "arms" or "leashes," onto inert polymer substrates in order to prepare blood-compatible materials. This work is covered in U.S. Pat. No. 3,826,678, issued July 30, 1974 and incorporated by reference herein. In particular, Hoffman et al. utilized mutual irradiation to graft hydroxyethyl methacrylate (HEMA) copolymers. Gombotz et al. (W. R. Gombotz et al., *J. Controlled Release* 2:375, 1985) and Venkataraman et al. (S. Venkataraman et al., *J. Biomed. Mat. Res.* 8:111, 1977) used a similar process to graft methacrylic acid (MAAc) or MAAc/HEMA copolymers. In each case, the grafted monomer was used to provide binding sites for subsequent chemical covalent binding of enzymes or drugs.

Using a different approach, some researchers have prepared polymeric gels for immobilization of enzymes and antibodies based on a co-monomer having a pendant active ester group. For example, Schnaar and Lee (R. L. Schnaar and L. C. Lee, *Biochem.* 14:1535, 1975) prepared the acrylic ester of N-hydroxyl succinimide (NSA), which they copolymerized with acrylamide and a cross-linker. Subsequent covalent bonding to an antibody produced an affinity gel. Adalsteinsson et al. (O. Adalsteinsson et al., *J. Mol. Cat.* 6:199, 1979) utilized this technique to immobilize enzymes. Lu and Feng (C. X. Lu and X. Feng, *J. Poly. Sci. Chem. Edi.* 18:2411, 1980) have used this technique by first preparing active ester monomers with different spacer arms, then copolymerizing them to produce a copolymer which has been used for immobilization of biomolecules.

The present invention describes a new method for immobilization of biomolecules, in which a monomer-conjugated biomolecule is grafted together with free monomer onto a hydrophilic, solid-phase polymeric substrate which has been pre-irradiated at low temperature. This method obviates the use of any initiators or catalysts which may detrimentally affect the biomolecule and reduce its activity. Advantageously, the methodology of the present invention provides for subsequent grafting of the biomolecule at very mild temperatures and pHs, and outside the radiation field, thus enhancing the activity of the immobilized biomolecule.

DISCLOSURE OF THE INVENTION

Briefly described, the present invention relates to the method of producing an immobilized biomolecule comprising the steps of exposing a solid-phase polymeric substrate to ionizing radiation at a temperature less than room temperature, and contacting the irradiated substrate with a biomolecule and free monomer in aqueous solution in a substantially oxygen-free atmosphere to form a graft copolymer, wherein the biomolecule is immobilized at least in part within the graft copolymer so formed.

A second aspect of the present invention is a method of producing an immobilized biomolecule comprising the steps of exposing a solid-phase polymeric substrate to ionizing radiation at a temperature less than room temperature, and contacting the irradiated substrate with a monomer-conjugated molecule and free monomer in aqueous solution in a substantially oxygen-free atmosphere to form a graft copolymer wherein the biomolecule is immobilized at least in part within the graft copolymer.

The present invention also discloses graft copolymers comprising a solid-phase polymeric substrate which is pre-irradiated at less than room temperature, and a biomolecule-monomer copolymer at least a portion of which is immobilized within the substrate.

A further aspect of the present invention discloses graft copolymers comprising a solid-phase polymeric substrate pre-irradiated at less than room temperature, and a monomer-conjugated biomolecule-monomer copolymer at least a portion of which is immobilized within the substrate.

In a preferred embodiment, the biomolecule can be an enzyme, catalyst, hormone, lectin, drug, vitamin, antibody, antigen, nucleic acid, DNA or RNA segment, pesticide, dye or fertilizer. The substrate can be selected from the group consisting of cellulose, argarose, sepharose, crosslinked dextran and their derivatives. These hydrophilic substrates are characterized by their ability to imbibe water, and can be used as layers on dip-sticks, unsupported sheets, particles, fibers, beads and the like. The ionizing radiation can be gamma rays produced by $^{60}Co$, high energy electrons from an electron accelerator, X-rays, or a radio frequency plasma discharge. The preferable temperature for conducting pre-irradiation of the substrate can range from less than room temperature to at least $-78°$ C. A hydrophilic monomer containing at least one vinyl or allyl group is preferred. Preferred monomers may be selected from the group shown in Table 1.

TABLE 1

WATER SOLUBLE MONOMERS cis-Aconitic acid
Acrylamide, 99.9%, triply recrystallized
Acrylamide, liquid concentrate, 30% w/v
Acrylamido glycolic acid
2-Acrylamido-2-methylpropanesulfonic acid
Acrylamidomethyl starch
Acrylic acid
N-Allylmethacrylamide
N-Benzylacrylamide
Bis-acrylylcystamine
iso-Butoxymethacrylamide
N-(Iso-Butoxymethyl)acrylamide 85%
N-Butylacrylamide
N-tert-Butylacrylamide
N-(t-Butyl)methacrylamide
2-Chloroacrylamide
Citraconic anhydride
N,N'-Cystaminebisacrylamide
Diacetone acrylamide
N,N-Diallylacrylamide
N,N-Di-n-butylacrylamide
N,N-Di(n-butyl)methacrylamide
N,N-Diethylacrylamide
Dihydroxyacetone
N,N'-(1,2-Dihydroxyethylene)-bisacrylamide
1,3-Dihydroxy-2-propanone
2,3-Dihydroxypropyl acrylate
2,3-Dihydroxypropyl methacrylate
N,N-Dimethylaminoethylmethacrylamide
3-N,N-Dimethylaminopropylmethacrylamide
N,N'-Dimethylenebisacrylamide
N,N-Dimethylmethacrylamide TABLE 1-continued

WATER SOLUBLE MONOMERS

N-(1,1-Dimethyl-3-oxybutyl)acrylamide
N,N'-Dodecanomethylenebisacrylamide
N-Dodecylmethacrylamide
N-Ethylmethacrylamide
Fluorescent Heperin
Glyceryl mono-acrylate
Glyceryl mono-methacrylate
N,N'-Hexamethylenebisacrylamide
2-Hydroxyethyl acrylate
2-Hydroxypropyl acrylate
Hydroxypropyl methacrylate
Itaconic acid
Methacrylamide
Methacrylic acid
Methacrylyl choline methyl sulfate, 40% aqueous
N-Methylacrylamide
N,N'-Methylenebisacrylamide, tech.
N-Methylmethacrylamide
N-Methylolacrylamide, 48% aqueous
p-Nitrophenyl acrylamide
N,N'-Nonamethylenebisacrylamide
N-(n-Octadecyl)acrylamide
N,N'-Octamethylenebisacrylamide
N-t-Octylacrylamide
N-Phenylacrylamide
N-Phenylmethacrylamide
N-iso-Propylacrylamide
Trimethylammoniumethyl methacrylate methosulfate 40% aqueous (1000 ppm MEHQ)
N,N'-Trimethylenebisacrylamide
m-Xylylenebisacrylamide Best Mode for Carrying Out the Invention The methods and immobilized biomolecules of the present invention are characterized by a high level of bioactivity, which is eroded in prior art techniques by use of direct radiation, high temperatures, high or low pH and/or catalysts or other initiator molecules, none of which are required in the present invention.

These methods and immobilized biomolecules are also characterized by an unusually high graft percent, thus providing a higher concentration of biomolecules per surface area of substrate. Additionally, low homopolymer formation is evidenced during grafting as compared to prior art methods, wherein the grafting step is performed at higher temperatures. Finally, the utilization of a monomer-conjugated biomolecule significantly enhances the extent of immobilization and activity of the biomolecule as compared to nonconjugated biomolecules.

To exemplify the present invention, immobilized L-asparaginase was produced. It is known that L-asparaginase is an effective therapeutic agent for certain malignant diseases, e.g., acute lymphoblastic leukemia, in which asparagine is an amino acid essential to the cancer cells which are dependent on a requisite levels of this amino acid. However, systemically injected asparaginase has a short half-life, so that it must be administered frequently. Repeated injections of foreign enzymes can elicit undesirable antibody responses and immunological reactions. As a possible solution to this problem, the immobilization of asparaginase into cellulose sheets is demonstrated.

To summarize the examples which follow, Example 1 describes the synthesis of N-hydroxy succinimide methacrylate ester (NSAM). Example 2 describes the preparation of monomer-conjugated asparaginase. Example 3 describes the pre-irradiation grafting methodology for immobilization of the biomolecule. Example 4 describes the protocol employed for assaying the asparaginase activity.

The following examples are offered by way of illustration, and not by way of limitation.

Example 1

Synthesis of N-Hydroxy Succinimide Methacrylate Ester (NSMA)

12.5 ml of 1,3-dicyclohexyl carbodiimide (DCCI; Aldrich, Milwaukee, WI) was added with stirring to a solution of 4.3 g methacrylic acid (MAAc) (0.05 mol, purified by distillation under pressure of 5 mm Hg at 50° C.) and 5.57 g N-hydroxysuccinimide (NHS) (0.05 mol; Sigma Chemical Co., St. Louis, MO) in 150 ml anhydrous tetrahydrofuran (THF; Baker Chemical Co., Phillipsburg, NJ) precooled to 0°-3° C., and the mixture was stirred for 2 more hours. The precipitate of N,N'-dicyclohexylurea was removed, 5 mg of 2,6-di-tert-butyl-4-methyl phenol (inhibitor; Aldrich) was added, and the filtrate was concentrated in vacuo to approximately 40 ml n-hexane (Baker), followed by quick warming to near boiling and filtering. The filtrate was set aside overnight at 4° C. and dried in vacuo, producing 5.3 g (58%) of colorless crystal which analyzed as NSMA using nuclear magnetic resonance (NMR). The reaction is as follows:

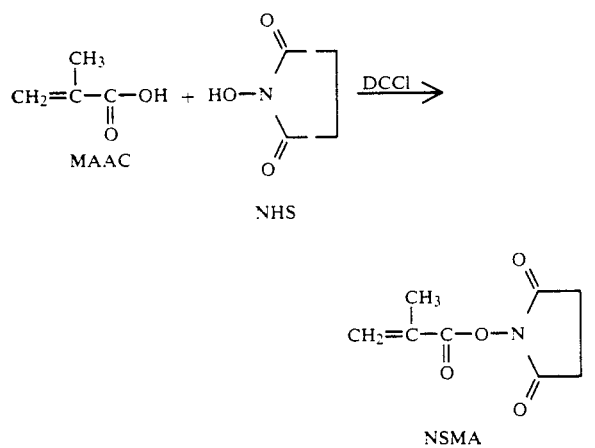

Example 2

Preparation of Monomer-Conjugated Asparaginase

Asparaginase (Merck & Co., Inc., Rahway, NJ) in 0.1 m TRIS buffer (tris hydroxymethyl axinomethane; Sigma) (1 ml of 4 mg protein/ml at pH 8.6) and NSMA (49.3 μl of 10 in dimethylformamide (DMF; Baker) are mixed together. The reaction mixture was stirred at room temperature for 3 hours. In order to terminate the reaction, the reaction mixture was added to a Pharmacia PD-10 (Sephadex G-25; Pharmacia Chemical Co., Piscataway, NJ) column which had been pre-equilibrated with at least 40 ml of 0.1 M TRIS. The monomer-conjugated enzyme was eluted off the column with 10 ml of the buffer, and the concentrated fractions were assayed for absorbance at 278 nm. The reaction is shown below. (For simplicity, only one monomer is shown conjugated to the enzyme.)

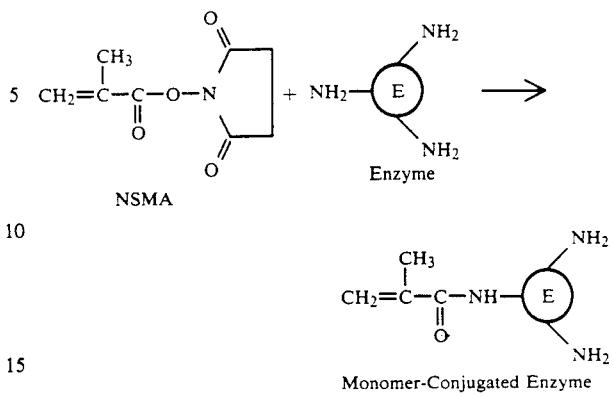

Example 3

Pre-Irradiation Grafting for Immobilization

Cellulose (#41 ashless filter paper, Whatman Ltd., City, State) sheet was used as the substrate polymer. Before pre-irradiation, the cellulose sheets were dried in an evacuated dessicator containing Anhydrone desiccant for 12 hours, and then weighed to obtain the original weight. The cellulose sheets were placed in test tubes with stoppers, and exposed to 2.67 Mrads from $^{60}$Co at a dose rate of 0.37 Mrads/hr, unless otherwise indicated. The radiation temperature was kept at −78° C. by immersing the tubes in a Dewar flask charged with dry ice and methanol.

After pre-irradiation, the tube containing the cellulose was evacuated. Then 6 ml of the grafting solution (20% acrylamide (AAm; electrophoresis grade, Aldrich) unless otherwise indicated) was sparged with nitrogen, and drawn into the tube containing the irradiated cellulose. The graft copolymerization was carried out at 0° C. for 2 hr, unless otherwise indicated. In the case of enzyme immobilization, 0.2 mg of the monomer-conjugated asparaginase in a 0.1 m TRIS buffer solution (pH 8.6) was added to the grafting solution just before drawing it into the tube. After grafting, the grafted cellulose was immersed in 0.1 M TRIS buffer (pH 8.6) for three days, during which period the buffer solution was changed six times. The data in Table 2 show that as the pre-irradiation temperature was raised from −78° C. to 0° C. and to room temperature (RT), the extent of post grafting at 0° C. diminished sharply.

TABLE 2

| Pre-irradiation Temperature (°C.) | Graft % (w/w) |
|---|---|
| RT | 3 |
| 0 | 10 |
| −78 | 657 |

Example 4

Enzyme Reaction

Prior to assaying enzyme activity, the immobilized enzyme sheets were washed with 50 ml of 1% (v/v) Triton X-100 (Rohm and Haas Co., Philadelphia, PA) solution in deionized H$_2$O for 15 min, then rinsed with deionized H$_2$O and three volumes of 50 ml 0.1 M TRIS, each for 15 min. The enzyme assay was carried out at 37° C. using a 0.02 M asparagine (Sigma) solution in 0.05 M TRIS buffer (pH 8.6) as the substrate. The enzyme activity was determined spectrophotometrically using the Nessler assay (R. H. Leonard, *Clin. Chem.,* 9:417, 1963)(Nessler reagent; Sigma) and a Bausch and Lomb Spectronic 1001.

Table 3 shows the effect of various grafting conditions on immobilized enzyme activity.

TABLE 3

The Effect of Grafting Conditions on Activity of Asparaginase Immobilized on Cellulose

| AAm Pre-irradiation Dose (Mrads)[a] | Asparaginase 0.2 mg protein/ 6 ml grafting solution | Graft[b] (%) ± S.D. | Asparaginase Activity per sheet (I.U. × 10 ± S.D.) |
|---|---|---|---|
| 20 | 0 | monomer-conjugated | 0 | 0.00 |
| 0 | 0 | monomer-conjugated | 0 | 0.00 |
| 20 | 2.67 | monomer-conjugated | 413 ± 74 | 1.08 ± 0.05 |
| 0 | 2.67 | monomer-conjugated | 5.5 ± 0.5 | 0.00 |
| 20 | 0 | native | 0 | 0.00 |
| 0 | 0 | native | 0 | 0.00 |
| 20 | 2.67 | native | 297 ± 6.5 | 0.19 ± 0.06 |
| 0 | 2.67 | native | 0 | 0.08 ± 0.01 |

[a]Dose rate = 10.3 rad/sec.
[b]Grafting was performed at 0° C. for 2 h. After grafting, the grafted cellulose was immersed in 0.1 TRIS buffer (pH 8.6).

Immobilization was carried out under different conditions. The data demonstrate that asparaginase is copolymerized to the grafted poly(AAm) chains, and not entrapped in the poly(AAm) or bound directly to the cellulose. Further, these data demonstrate that the presence of AAm is required, and that the cellulosic substrate must be pre-irradiated in order to achieve enzyme activity. Monomer-conjugated asparaginase produces approximately sixfold greater activity per sheet than native unconjugated enzyme. While some activity is shown for native enzyme in the absence of AAm, this activity is relatively insignificant.

The protocol described in the preceding examples could be modified by one skilled in the art to employ other biomolecules. For example, antibody could be immobilized onto cellulose by utilizing the pre-irradiation techniques set forth herein. This procedure is illustrated by the following reaction:

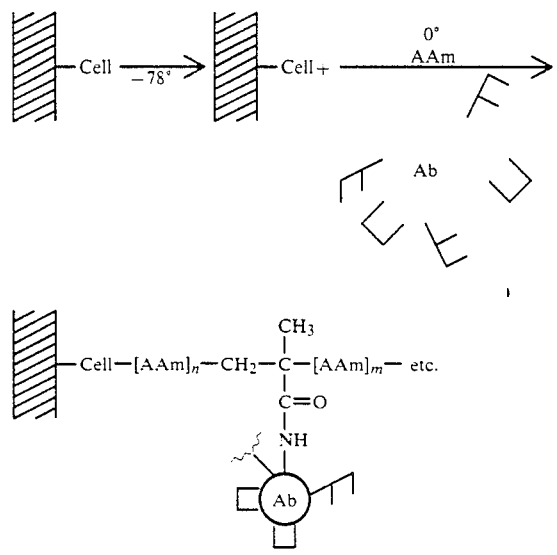

These experiments show that pre-irradiation of cellulose in air at low temperatures can produce trapped radicals, which can then be used to graft copolymerized monomer-conjugated biomolecules together with free vinyl monomer without any initiator or catalyst. Unusually high levels of grafting may be obtained by pre-irradiation in air at −78° C., followed by grafting in a nitrogen atmosphere at 0° C. These conditions preserve the biomolecule activity. The immobilized biomolecule is stable and retains its activity after storage for many days at 4° C. This new process may be used to immobilize a wide variety of biomolecules, such as enzymes, catalysts, hormones, lectins, drugs, vitamins, antibodies, antigens, nucleic acids, DNA and RNA segments, pesticides, dyes and fertilizers. Biologically active supports produced by this process may be utilized for a wide variety of therapeutic or diagnostic applications, as well as for bioseparation in general.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method of producing an immobilized biomolecule comprising the steps of:
   exposing a solid-phase polymeric substrate to ionizing radiation at a temperature between about 0° C. to about −78° C.; and
   contacting the irradiated substrate with a biomolecule and free monomer, in aqueous solution in a substantially oxygen-free atmosphere at a temperature less than the temperature at which the biomolecule inactivates, to form a graft copolymer, wherein the biomolecule is immobilized at least in part within the graft copolymer.

2. The method of claim 1 wherein the biomolecule is an enzyme.
3. The method of claim 2 wherein the enzyme is asparaginase.
4. The method of claim 1 wherein the biomolecule is a catalyst.
5. The method of claim 1 wherein the biomolecule is an antibody.
6. The method of claim 1 wherein the biomolecule is an antigen.
7. The method of claim 1 wherein the biomolecule is a drug.
8. The method of claim 1 wherein the biomolecule is a hormone.
9. The method of claim 1 wherein the biomolecule is a pesticide.
10. The method of claim 1 wherein the biomolecule is a fertilizer.
11. The method of claim 1 wherein the biomolecule is an insecticide.
12. The method of claim 1 wherein the biomolecule is a dye.
13. The method of claim 1 wherein the biomolecule is a vitamin.
14. The method of claim 1 wherein the biomolecule is a single or double stranded sequence of DNA or RNA.
15. The method of claim 1 wherein the biomolecule is a nucleic acid.
16. The method of claim 1 wherein the substrate is hydrophilic.

17. The method of claim 1 wherein the substrate is a polysaccharide.

18. The method of claim 1 wherein the substrate is selected from the group consisting of cellulose, agarose, sepharose and cross-linked dextran.

19. The method of claim 1 wherein the source of ionizing radiation is $^{60}$Co.

20. The method of claim 1 wherein the source of ionizing radiation is X-rays.

21. The method of claim 1 wherein the source of ionizing radiation is high-energy electrons.

22. The method of claim 1 wherein the source of ionizing radiation is radio frequency plasma gas discharge.

23. The method of claim 1 wherein a substrate is exposed to ionizing radiation at −78° C.

24. The method of claim 1 wherein the monomer is characterized by having at least one vinyl group.

25. The method of claim 1 wherein the monomer is characterized by having at least one allyl group.

26. The method of claim 1 wherein the monomer is selected from the group shown in Table 1.

27. A method of producing an immobilized biomolecule comprising the steps of:
    exposing a solid-phase polymeric substrate to ionizing radiation at a temperature between about 0° C. to about −78° C.; and
    contacting the irradiated substrate with a monomer-conjugated biomolecule and free monomer, in aqueous solution in a substantially oxygen-free atmosphere at a temperature less than the temperature at which the biomolecule inactivates, to form a graft copolymer, wherein the biomolecule is immobilized at least in part within the graft copolymer.

28. The method of claim 27 wherein the biomolecule is an enzyme.

29. The method of claim 28 wherein the enzyme is asparginase.

30. The method of claim 27 wherein the biomolecule is a catalyst.

31. The method of claim 27 wherein the biomolecule is an antibody.

32. The method of claim 27 wherein the biomolecule is an antigen.

33. The method of claim 27 wherein the biomolecule is a drug.

34. The method of claim 27 wherein the biomolecule is a hormone.

35. The method of claim 27 wherein the biomolecule is a pesticide.

36. The method of claim 27 wherein the biomolecule is a fertilizer.

37. The method of claim 27 wherein the biomolecule is an insecticide.

38. The method of claim 27 wherein the biomolecule is a dye.

39. The method of claim 27 wherein the biomolecule is a vitamin.

40. The method of claim 27 wherein the biomolecule is a single or double stranded sequence of DNA or RNA.

41. The method of claim 27 wherein the biomolecule is a nucleic acid.

42. The method of claim 27 wherein the substrate is hydrophilic.

43. The method of claim 27 wherein the substrate is a polysaccharide.

44. The method of claim 27 wherein the substrate is selected from the group consisting of cellulose, agarose, sepharose and cross-linked dextran.

45. The method of claim 27 wherein the source of ionizing radiation is $^{60}$Co.

46. The method of claim 27 wherein the source of ionizing radiation is X-rays.

47. The method of claim 27 wherein the source of ionizing radiation is high-energy electrons.

48. The method of claim 27 wherein the source of ionizing radiation is a radio frequency plasma gas discharge.

49. The method of claim 27 wherein a substrate is exposed to ionizing radiation at −78° C.

50. The method of claim 27 wherein the monomer is characterized by having at least one vinyl group.

51. The method of claim 27 wherein the monomer is characterized by having at least one allyl group.

52. The method of claim 278 wherein the monomer is selected from the group shown in Table 1.

* * * * *

UNITED STATES PATENT AND TRADEMARK OFFICE
CERTIFICATE OF CORRECTION

PATENT NO. : 5,034,428

DATED : July 23, 1991

INVENTOR(S) : Allan S. Hoffman; Liang C. Dong

It is certified that error appears in the above-identified patent and that said Letters Patent is hereby corrected as shown below:

In column 10, claim 52, line 44, please delete "278" and substitute therefor -- 27 --.

Signed and Sealed this

First Day of December, 1992

Attest:

DOUGLAS B. COMER

Attesting Officer

Acting Commissioner of Patents and Trademarks